United States Patent [19]

Folkman et al.

[11] Patent Number: 4,994,443
[45] Date of Patent: Feb. 19, 1991

[54] INHIBITION OF ANGIOGENESIS

[75] Inventors: Moses J. Folkman, Brookline; Stephanie Taylor, Boston; Robert S. Langer, Somerville, all of Mass.

[73] Assignee: The Children's Medical Center Corporation, Boston, Mass.

[21] Appl. No.: 257,409

[22] Filed: Oct. 13, 1988

Related U.S. Application Data

[60] Division of Ser. No. 80,255, Jul. 27, 1987, abandoned, which is a continuation of Ser. No. 844,221, Mar. 24, 1986, abandoned, which is a continuation of Ser. No. 641,305, Aug. 16, 1984, abandoned, which is a continuation-in-part of Ser. No. 559,175, Dec. 7, 1983, abandoned, which is a continuation-in-part of Ser. No. 451,431, Dec. 20, 1982, abandoned.

[51] Int. Cl.$^5$ .................... A61K 31/725; A61K 31/56
[52] U.S. Cl. ...................................... 514/56; 514/177; 514/178
[58] Field of Search .......................... 514/56, 177, 178

[56] References Cited

U.S. PATENT DOCUMENTS 4,771,042 7/1989 Braughler et al. .................. 514/171

OTHER PUBLICATIONS

The Merck Index, 9th edition, 1976, pp. 629–630 & 999.
Elias et al., Cancer Chemotherapy Reports, Part 1, vol. 56, No. 6, 12/72, pp. 783–785.
Elias et al., Cancer, 7/75, vol. 36, pp. 129–136.
Eichbaum Rev. Bras. de Pesquisas Med. Biol. 8(5–6): 489–496, 1975.
Grossman et al., Proc. Natl. Acad. Sci. U.S.A., vol. 78, 1176–1180 (1981).

*Primary Examiner*—Stanley J. Friedman
*Assistant Examiner*—Raymond J. Henley, III
*Attorney, Agent, or Firm*—Fish & Richardson

[57] ABSTRACT

Angiogenesis in mammals is inhibited by administration of the active agents (1) heparin or a heparin fragment which is a hexasaccharide or larger or analogous compounds and (2) a steroid having 17α- and 21-hydroxy groups, 3- and 20-one groups, and in the 16-position hydrogen hydroxy or a methyl group, and non-toxic physiologically acceptable carboxylates, acetals, ketals and phosphates thereof.

15 Claims, No Drawings

INHIBITION OF ANGIOGENESIS

This invention was made with U.S. Government support and the Government has certain rights in the invention.

This application is a divisional of U.S. Ser. No. 07/080,255 filed July 27, 1987, now abandoned which is a continuation of U.S. Ser. No. 06/844,221 filed Mar. 24, 1986, now abandoned which is a continuation of U.S. Ser. No. 06/641,305 filed Aug. 16, 1984 now abandoned which is a continuation-in-part of U.S. Ser. No. 559,175 filed Dec. 7, 1983 which is in turn a continuation-in-part of U.S. Ser. No. 451,431 filed Dec. 20, 1982, now abandoned.

This invention relates to inhibition of angiogenesis and pertains more specifically to treatment of mammals with heparin or heparin fragments or analogues and with steroids to inhibit angiogenesis with subsequent regression of large tumor masses and prevention of tumor metastasis in mammals containing such tumors.

Angiogenesis, the growth of new capillary blood vessels, is important in normal processes such as development of the embryo, formation of the corpus luteum and wound healing. It is also a component in pathologic processes such as chronic inflammation, certain immune responses and neoplasia. Furthermore, angiogenesis is a property of most solid tumors and is necessary for their continued growth.

It has previously been reported that heparin enhanced the intensity of angiogenesis induced by tumors in vivo, although in the absence of tumor cells or tumor extract neither heparin nor the mast cells which release heparin could induce angiogenesis. Taylor and Folkman, Nature Vol. 297, 307–312 (1982). It has also been reported in Shubik et al., J. Natl. Cancer Inst., Vol. 57, 769–774 (1976) that 6 α-methyl-prednisolone partially suppressed tumor angiogenesis in hamster cheek pouch under certain conditions, but tumor growth was not stopped, and many other publications have reported continued growth of tumors even in the presence of large doses of cortisone. It has also been reported in Gross et al., Proc. Natl. Acad. Sci., U.S.A., Vol. 78, 1176–80 (1981) that medroxyprogesterone, dexamethasone, and to a lesser extent cortisone, inhibited tumor angiogenesis in rabbit corneas, while estradiol and testosterone were ineffective Heparin, an α,β glycosidically linked highly sulfated copolymer of uronic acid and glucosamine, has been used clinically as an anticoagulant for half a century. Despite its importance and widespread use, both the exact structure of heparin and the precise nature by which it acts in blood anticoagulation have not been elucidated. Much of the difficulty in determining the structure of heparin is because it is not a homogeneous substance. Heparin is polydisperse with a molecular weight range from 5,000 to 40,000. Within a given chain, there are also structural variations such as varying degrees of sulfation, N-acetylation, and C-5 epimerization in the uronic acid residue.

Consequently, the precise composition of commercial heparin varies depending on its source and method of purification. Heparin has been degraded by treatment with heparinase (an enzyme of bacterial origin, Langer et al. U.S. Pat. No. 4,341,869) which cleaves the molecule at the α-glycosidic linkages between N-sulfated-D-glucosamine 6-sulfate and L-iduronic acid 2-sulfate to form fragments including disaccharide, tetrasaccharide, hexasaccharide, and larger oligosaccharides, each being simply a chain-shortened heparin fragment with minor end group modification (the degradation results in a Δ-4,5 site of unsaturation in the terminal uronic acid residue). Linhardt et al., J. Biol. Chem., Vol. 257, 7310-13 (1982).

It has now been found that angiogenesis in mammals is inhibited and tumor masses in mammals are caused to regress (and metastasis prevented) by administration of the combination of two essential active agents: (1) heparin or a heparin fragment which is a hexasaccharide or larger, or an analogous compound having one of the structures

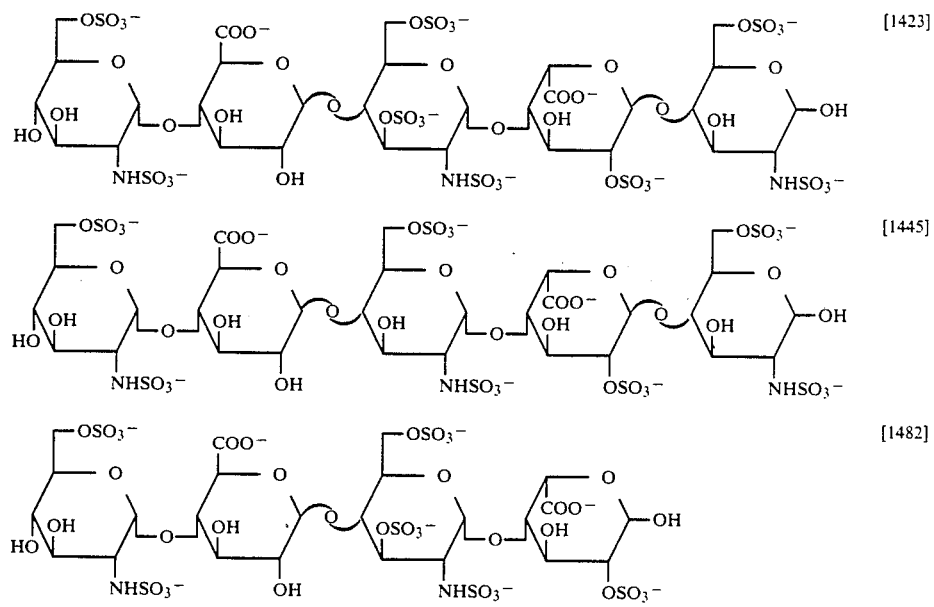

and (2) a steroid having 17α- and 21-hydroxy groups, 3- and 20-one groups, and in the 16- position hydrogen hydroxy or a methyl group, and non-toxic physiologically acceptable carboxylates, acetals, ketals and phosphates thereof, said combination exhibiting a vascular zone when implanted in an immature chick chorioallantoic membrane.

Among the steroids which are effective are the following:

17α,21-dihydroxy-4-pregnene-3,11,20-trione and its 21-acetate (or cortisone)
11α, 17,21-trihydroxypregn-4-ene-3,20-dione (or 11α-hydrocortisone)
11β,17α,21-trihydroxypregn-4-ene-3,20-dione (or hydrocortisone)
17α,21-dihydroxypregna-4,9(11)-diene-3,20-dione
15α,17α,21-trihydroxy-4-pregnene-3,20-dione
16α,17α,21-trihydroxy-6α-methylpregn-4-ene-3,20-dione-21-acetate-16,17 cyclic ketal of acetone
6α-fluoro-17α,21-dihydroxy-16β-methylpregna-4,9(11)-diene-3,20-dione
6α-fluoro-17α,21-dihydroxy-16β-methylpregna-4,9(11)-diene-3,20-dione-17,21-diacetate
6β,17α,21-trihydroxypregn-4-ene-3,20-dione
17α,21-dihydroxypregn-4-ene-3,20-dione-21-acetate
17α,21-dihydroxypregn-4-ene-3,20-dione
9β,11β-epoxy-17α,21-dihydroxy-2α-methylpregn-4-ene-3,20-dione-21-acetate
17α,21-dihydroxy-16α-methylpregn-4-ene-3, 20-dione
9α,11β-dichloro-17α,21-dihydroxypregn-4-ene-3,20-dione-21-acetate
17α,21-dihydroxy-6α,16α-dimethylpregn-4-ene-3,20-dione-21-acetate
17α,21-dihydroxy-16α-methylpregna-4,9(11)-diene-3,20-dione-21-acetate
17α,21-dihydroxy-16β-methylpregna-4,9(11)-diene-3,20-dione-21-benzoate
17α,21-dihydroxy-6β-methylpregna-4,9(11)-diene-3,20-dione-21-acetate
6α-fluoro-17α,21-dihydroxy-16β-methylpregna-4,9(11)-diene-3,20-dione-17-acetate-21-benzoate
17α,21-dihydroxy-16β-methylpregna-1,4, 9(11)-triene-3,20-dione-17-succinate sodium monohydrate
9α-fluoro-11β,16α,17α,21-tetrahydroxypregn-4-ene-3,20-dione-16,21-diacetate
17α,21-dihydroxy-16α-methylpregna-1,4,9(11)-triene-3,20-dione-21-succinate sodium monohydrate
6α-fluoro-17α,21-dihydroxy-16β-methylpregna-1,4,9(11)-triene-3,20-dione-21-succinate sodium More preferred are those steroids which lack glucocorticoid and mineralo-corticoid activity, since such activity is an undesired side effect and limits the dose size or extent of use of the steroid for the purpose of the present invention. Among such more preferred steroids are 11α, 17,21-trihydroxypregn-4-ene-3,20-dione (or 11α-hydrocortisone), 17α,21-dihydroxypregn-4-ene-3,20-dione (or 11-desoxycortisol or Cortexolone), and 17α,21-dihydroxypregna-4,9(11)-diene-3,20-dione.

It has also been found that certain steroids which display much greater glucocorticoid activity than hydrocortisone, for example 11β,17α,21-trihydroxy16α-methyl-9α-fluoropregna-1,4-diene-3,20-dione (also known as dexamethasone) and 11β,17α,21-trihydroxypregna-1,4-diene-3,20-dione (also known as prednisolone) are inactive for the purposes of the present invention.

Neither mature non-growing blood vessels nor vascular tissue seems to be affected by the procedure of the present invention. Inhibition of angiogenesis in accordance with the present invention, in addition to its effect upon tumor regression and metastasis in tumor-bearing mammals, is effective as a contraceptive in females even if first administered after insemination has occurred, and is effective in treating diseases involving neovascularization such as neovascular diseases of the eye.

None of the steroids themselves effectively inhibits angiogenesis nor causes regression of tumors in the absence of heparin or a heparin fragment or the specified compounds. Heparin alone does not inhibit angiogenesis but on the contrary enhances it.

The active agents may be mixed together prior to administration or may be administered separately at about the same time so that both are present simultaneously in the mammal being treated. The administration may be oral or parenteral including inter alia topical application, intravenous, intra-arterial or subcutaneous injection, and including absorption as well as injection and introduction into bodily apertures or orifices In the case of heparin, which is commercial available in the form of heparin sodium, oral administration leads to degradation in the gastrointestinal tract which results in loss of its anticoagulant activity, but because it has been found that the degradation products include disaccharide and larger fragments, this mode of administration is highly effective for the present invention both for heparin for heparin fragments, and for the specified compounds. The heparin and its fragments as well as the specified compounds may be employed in any physiologically acceptable non-toxic form, including their metal salts, preferably as the sodium salts, all of which are embraced in the term "heparin" or "fragment" or "compound" as used in the present specification and claims. For best results heparin sold under the trade name "Panheprin" (Abbott Laboratories) is preferred, but heparin from other sources, such as Hepar, Inc. can also be used although less effective Cortisone and its physiologically acceptable non-toxic derivatives such as the acetate, as well as many other steroids useful in the present invention, are only very slightly soluble in water, hence are preferably administered parenterally, e.g. subcutaneously, not orally. For oral administration, steroids such as hydrocortisone or its 11-α isomer (which are relatively water soluble as compared to cortisone) or one of their water-soluble physiologically acceptable non-toxic derivatives such as a carboxylate, acetal, ketal or the phosphate are preferred Water-insoluble derivatives of water-soluble steroids such as derivatives of hydrocortisone or its 11-α isomer which are non-toxic and physiologically acceptable, are administered parenterally. The terms "cortisone" and "hydrocortisone" and 11- α isomer of hydrocortisone as used in the present specification and claims are intended to include both the steroids themselves and their derivatives as defined above.

Dosages employed are limited only by the well known limits for the administration of the drugs individually for their usual effects, in the case of cortisone, hydrocortisone, or its 11-α isomer. However, a number of the useful steroids have no other biological effect apart from the present invention. Simple testing, for example, by the procedure of Example 3 below, suffices to determine effectiveness and optimum dose. Heparin may be administered percutaneously in amounts as large as tolerable without objectionable anticoagulant effects. Since heparin administered orally has no anticoagulant effect, and since the hexasaccharide fragment has no anticoagulant effect whether given orally or in any other way, large dosages can thus be administered without risk of bleeding. Oral dosages of heparin of the order of 27,000–45,000 units per kg. body weight per day have been found to be effective, but when administered subcutaneously, doses greater than about 600 units per kg. body weight twice daily led to undesirable anticoagulation effects. In the case of the hexasaccharide fragment, 7 mg per kg. body weight twice daily subcutaneously has been found effective. Cortisone acetate was effective in subcutaneous dosages of 250 mg/kg/day down to 37 mg/kg/day and hydrocortisone was effective orally in amounts of 0.45 mg/ml drinking water (approximately 75 mg/kg/day). The 11-α isomer of hydrocortisone is approximately equal to hydrocortisone in activity for the purpose of the present invention.

The dose size required to bring about regression of tumors or to prevent metastasis varies to some extent depending upon the identity of the tumor, as does the length of time required to bring about complete regression of tumors. Tumor size at the beginning of treatment also affects the length of time required for complete regression. Because of the occurrence of angiogenesis in psoriasis and arthritis, it is expected that the present invention may be useful in treating these diseases. Because administration of cortisone, with or without heparin or heparin fragments or the specified compounds, may result in pulmonary infection after a number of days, it is desirable to administer a suitable antibiotic as prophylaxis during treatment in accordance with the present invention.

The active agents are best dissolved or suspended in a suitable carrier which itself must be non-toxic and physiologically acceptable, such as water or normal saline. Compositions containing mixtures of the active agents, either dry or in a suitable carrier, can be employed.

EXAMPLE 1

Cortisone acetate 0.9 mg in 0.9 ml saline was flooded over the chorioallantoic membrane of 8-day chick embryos through a window in the shell made previously. On day 9, tumor extract (100 μg) from hepatoma cells (as described in Zetter, Nature Vol. 285, 41–43, 1980) in 5 μl H$_2$O was placed on the center of a round 15 mm diameter plastic coverslip and allowed to dry. To the center of each coverslip was then added a 5 μl aliquot containing either heparin (6 μg, i.e., 1 unit), or water, at least twenty embryos being subjected to each. After drying, the coverslip was placed on the chorioallantoic membrane: Additional control embryos received tumor extract and/or heparin, but were not pre-treated with cortisone acetate. The membranes were viewed on day 11 with a ×12 stereoscope. Angiogenesis was present if new capillaries were seen to converge on the spot in the center of the coverslip. All of the embryos treated with water or heparin but no cortisone exhibited angiogenesis, as well as 80% of those treated with cortisone acetate alone. Less than 2% of those treated with both heparin and cortisone acetate exhibited angiogenesis.

EXAMPLE 2

Porcine mucosal heparin was exhaustively degraded using heparinase by the procedure of Langer et al, Science Vol. 217, 261-3 (1982) and the products were fractionated using Sephadex columns equilibrated with 1M NH$_4$OAc. The degraded heparin had no anticoagulant activity as determined by activated partial thromboplastic time or whole blood recalcification time. The product or product mixture (250 mg) was dissolved in 1 cc of 1M NH$_4$OAc, loaded onto a 75×2.5 cm G-15 column, and eluted at 0.5 cc/min. This resulted in several incompletely resolved peaks corresponding to tetra-, hexa-, and higher oligosaccharides and a separate peak corresponding to disaccharide product. The disaccharide peak was freeze-dried, dissolved in 0.2 cc of 1M NH$_4$OAc and rechromatographed on G-15 resulting in the same sharp peak which was freeze-dried. The mixture of tetra-, hexa-, and oligosaccharides was freeze-dried, redissolved in 1 cc of 1M NH OAc, and eluted from a 50×1.25 cm G-50 at 2 cc/min, resulting in an unresolved double peak corresponding to tetra- and hexasaccharide fragments and an additional peak corresponding to oligosaccharides which was freeze-dried. The tetra- and hexasaccharide fragments were combined, freeze-dried, redissolved in 1 cc of 1M NH$_4$OAc, and loaded onto a G-15 column. The tetrasaccharide was eluted from a G-15 column in a single peak, the center cut of which was freeze-dried. The hexasaccharide fraction was freeze-dried, redissolved in 0.3 cc 1M NH$_4$OAc, eluted from a G-15 column in a single peak, the center cut of which was freeze-dried.

Fragment size was determined by dissolving a weighed amount of each fraction into 0.03M hydrochloric acid and measuring the absorbance of this solution at 232 nm. The molecular weight of each fragment was calculated using a molar absorptivity, for the α, β unsaturated carboxylate end group present in each of these products, of $\xi=5500$. The di- and tetrasaccharides were further characterized by comparing their K avg-values on G-15 with mono-, di-, and trisaccharide standards. Measured molecular weights were 530, 1210, 1600, and 1870 for the di-, tetra-, hexa-, and oligosaccharide fractions respectively.

The various heparin fragments were dissolved into methylcellulose discs either alone or with cortisone acetate. The discs were then applied to the 4-day yolk sac membrane of chick embryos cultured in Petri dishes as described by Taylor and Folkman, Nature, Vol. 297, 307–312 (1982). In the presence of cortisone acetate (100 μg), as shown in the following table, the hexasaccharide fragment demonstrated the highest antiangiogenesis activity.

TABLE I

Percent Embryos That Developed Avascular Zones 48 Hours After Implantation of Methylcellulose Discs On The 4-day Old Yolk Sac Membrane

| CONC. (μg) | OLIGO-SAC-CHARIDES | HEXA-SAC-CHARIDE | TETRA SAC-CHARIDE | DI-SAC-CHARIDE |
|---|---|---|---|---|
| 12 | all died | 100% | 0% | 0% |
| 8 | 100% | 100% | | |
| 4 | 25% | 100% | | |
| 1 | 25% | 50% | | |
| 0.1 | 0 | 50% | | |

Tetra- and disaccharides were inactive. Oligosaccharides were less active and were toxic at higher concentrations. Therefore, the hexasaccharide fragment was used in subsequent experiments. In the growing 6-day chorioallantoic membrane, discs containing hexasaccharide (12 μg) and cortisone acetate (100 μg) produced large avascular zones up to 12.6±0.1 mm diameter by 48 hours. As in the case of heparin (with cortisone acetate), capillaries in the mesodermal layer were absent while the other two tissue layers of the membrane were intact and viable. Hexasaccharide alone did not promote tumor angiogenesis as heparin did.

All discs contained a combination of cortisone acetate (100 μg) and a heparin fragment. No avascular zones developed in the presence of any heparin fragment alone, or with cortisone or methylcellulose alone. Ten embryos were used for each group. With hexasaccharide (plus cortisone), the area of the avascular zone was 17% of the vascular membrane at 12 μg and 15% at 0.1 μg. For the oligosaccharides, the maximum avascular area was 10%.

EXAMPLE 3

Fertilized chick embryos were removed from their shell on day 3 (or 4) and incubated in a Petri dish in high humidity and 5% $CO_2$ as previously described by Auerbach et al., J. Devel. Biol., Vol. 41, 391–4 (1974), except that an outer dish and antibiotics were not used. On day 6, a methylcellulose disc (10 μl) containing either heparin (6 μg), or hexasaccharide heparin fragment (12 μg), or cortisone acetate (Sigma, powder free of preservatives and suspending agents), or a combination of cortisone acetate+heparin or cortisone acetate+hexasaccharide was implanted on the chorioallantoic membrane. The embryos were examined 48 hours later, and if a clear avascular zone appeared around the methylcellulose disc, the diameter of the zone was measured with a Nikon Profile projector at ×20. Thirty embryos were used in each group. India ink was injected into the heart of some embryos just before formalin fixation so that vessels could be followed to the edge of the avascular zone in histological sections.

Hexasaccharide+cortisone acetate produced avascular zones of 12.6±0.1 mm diameter in all embryos. Heparin+cortisone acetate produced avascular zones of 8.9±0.7 mm diameter. There were no avascular zones in the presence of any compounds alone, or with methylcellulose alone.

Histologic cross-sections of the chorioallantoic membranes, revealed that capillaries developed normally in the presence of any compound alone. In contrast, capillaries were completely absent from the mesodermal layer in the face of either hexasaccharide+cortisone acetate, or heparin+cortisone acetate, while the ectodermal and endodermal cell layers remained unaffected. In the mature chorioallantoic membrane where vessels are no longer growing, the cortisone acetate-heparin or -hexasaccharide fragment combinations were without effect.

Avascular zones were also observed using essentially the same procedure with a combination of heparin (Panheprin) (10 units) with 25–200 μg of each of the following steroids:

11β, 17α, 21-trihydroxypregn-4-ene-3,20-dione
11α, 17α, 21-trihydroxypregn-4-ene-3,20-dione
17α,21-dihydroxypregn-4-ene-3,20-dione
17α,21-dihydroxypregna-4,9(11)-diene-3,20-dione
9α-fluoro-11α,16α,17α,21-tetrahydroxypregna-1,4-diene-3,20-dione (or triamcinolone)
9α,11β-dichloro-17α,21-dihydroxypregn-4-ene-3,20-dione-21-acetate
17α,21-dihydroxy-16β-methylpregna-4,9(11)-diene-3,20-dione-21-benzoate
17α,21-dihydroxy-16β-methylpregna-1,4,9(11)-triene-3,20-dione-21-succinate sodium monohydrate
6α-fluoro-17α,21-dihydroxy-16β-methylpregna-4,9(11)-diene-3,20-dione
6α-fluoro-17α,21-dihydroxy-16β-methylpregna-4,9(11)-diene-3,20-dione-17,21diacetate
15α,17α,21-trihydroxy-4-pregnene-3,20-dione
16α,17α,21-trihydroxy-6α-methylpregn-4-ene-3,20-dione-21-acetate-16,17-cyclic ketal of acetone Of the foregoing, the last four displayed the greatest anti-angiogenic activity by this test.

All of the effective combinations of active agents, for the purposes of the present invention, exhibit an avascular zone when implanted on an immature chick chorioallantoic membrane as described in this Example 3.

EXAMPLE 4

Polymer pellets of ethylene vinyl acetate copolymer (EVA) of approximately 1 mm diameter were impregnated, using the procedure of Langer et al., Nature, Vol. 263, 797–800 (1976), with heparin 180 μg (Sigma), or hexasaccharide fragment 300 μg, or cortisone acetate 1.5 mg (Sigma), or a combination of cortisone and heparin. The pellets were implanted in the cornea of a rabbit eye 1 mm from the limbus and a 1 $mm^3$ piece of V2 carcinoma was implanted distal to the polymer, 2 mm from the limbus. In the opposite eye of each rabbit, control pellets that were empty were similarly implanted in juxtaposition to the tumor.

Release rates averaged 15 μg/day for heparin; 21 μg/day for hexasaccharide fragment; and 5 μg/day for cortisone. When the compounds were mixed, they released at the same rates. By spectrophotometry, the pellets released heparin for 14 days, hexasaccharide for 11 days, and cortisone for more than 30 days.

As capillary blood vessels grew towards the tumor implant, maximum vessel length was measured every 3 days with a stereoscopic slit lamp at ×10 (±0.1 mm). On day 14 the rabbits were killed, and India ink was injected into each carotid artery. The corneas were removed and examined with a stereoscope.

New capillary blood vessels were observed growing towards the tumor and passing over an empty pellet or a pellet containing heparin alone at a mean rate of 0.44 mm/day; and over a pellet containing cortisone alone at 0.22 mm/day. The tumors behind these pellets were vascularized by 6–8 days. When the pellets contained both cortisone and heparin, there was no capillary growth for 13 days. When the heparin-cortisone pellets were removed or when the pellets were depleted of heparin, capillary growth resumed. Histologic sections showed that tumor cells remained viable and capable of replication even when they were adjacent to the heparin-cortisone pellet.

In the presence of implanted pellets in which the hexasaccharide fragment of Example 2 replaced the heparin, new capillaries grew toward the tumors at a mean rate of 0.30 mm/day in the presence of the hexasaccharide pellets; 0.14 mm/day when the pellets contained cortisone; and 0.32 mm/day when the pellets were empty. In the presence of the hexasaccharide-cortisone combination, there was no capillary growth throughout the 13-day observation period in 4 rabbits, and in one rabbit a few capillaries grew at 0.07 mm/day.

EXAMPLE 5

(a) Reticulum cell Sarcoma: 1 $mm^3$ pieces of tumor were implanted with a trocar subcutaneously in the backs of 30 mice; 5 per group. Treatment was begun 10 days later, when mean tumor volume was $1.5 \times 10^2$ $mm^3$. Oral heparin was 200 U/ml in drinking water, average daily consumption was 5–10 ml water per 22 g mouse. Cortisone acetate was administered subcutaneously once daily in a dose of 250 mg/kg for six days, 125 mg/kg for one day, 75 mg/kg for one day, and thereafter a daily maintenance dose of 37 mg/kg (a "tapered" dosage). Control animals received either saline injections, or heparin alone or cortisone acetate alone. All controls were dead by day 34 with large primary tumors and lung metastases. All mice treated with oral heparin+cortisone tapered dosage became tumor-free by day 15 and remained so after treatment was discontinued.

An additional group of mice was treated similarly except that heparin was administered twice daily subcutaneously in a dose of 627 units, and cortisone acetate was administered subcutaneously once daily in a uniform dose of 75 mg/kg. Response of the mice was the same as in the first set except that tumors recurred after cessation of treatment; these mice became permanently tumor-free when subjected to the regimen of oral heparin and cortisone acetate tapered dosage described above. One of these mice died on day 31 with no gross primary tumor and no metastases.

(b) Lewis Lung Carcinoma: Treatment began 7 days after implantation of a 1 mm$^3$ piece of tumor in 42 mice: 7 per group. Treatment was with oral heparin and subcutaneous cortisone acetate tapered dosages described above. All controls died by day 33 with large tumors and numerous lung metastases. In the heparin+cortisone acetate groups treatment was discontinued for each mouse after tumor had been invisible for approximately 7 days. In the oral heparin+cortisone acetate all mice were off treatment by day 33, and remained tumor-free. In an additional group treated with subcutaneous heparin and subcutaneous cortisone acetate (75 mg/kg), 5 mice were off treatment at day 37 and remained tumor-free. Two mice died of pneumonia on days 30 and 33 respectively with small primary tumors (<75 mm$^3$). One metastasis was found in one mouse.

To determine if other steroids could substitute for cortisone, heparin was administered with hydrocortisone, dexamethasone, or medroxyprogesterone. Only hydrocortisone was as effective as cortisone acetate in causing tumor regression when administered with heparin. At the highest tolerable doses neither dexamethasone (3.2 mg/Kg), nor medroxyprogesterone (112 mg/Kg), caused regression of Lewis lung tumors with or without heparin.

(c) B-16 Melanoma: $7.4 \times 10^6$ melanoma cells were injected subcutaneously into 40 mice; 5 per group. Treatment of one group was with oral heparin as described above and oral hydrocortisone, 0.45 mg/ml in drinking water Another group received oral heparin and subcutaneous cortisone acetate tapered dosage, and a third group received subcutaneous heparin and cortisone acetate 75 mg/kg. Controls received either water, or heparin alone, or hydrocortisone or cortisone acetate alone. All control animals died by day 31 with large tumors and lung metastases. In the heparin+cortisone acetate groups, treatment was discontinued after tumor had become invisible for approximately 7 days. In the oral heparin+cortisone acetate tapered dosage group, 1 mouse died on day 24 with a partially regressed tumor and 2 lung metastases that were avascular and measured less than 0.1 mm. All other mice in the group became tumor-free and remained so after their treatment was discontinued by day 32. In the subcutaneous heparin+cortisone acetate group one mouse died on day 18 and another on day 21; neither had lung metastases. Treatment was discontinued for the other 3 mice on day 32; tumors 3 weeks later were successfully re-treated with oral heparin+cortisone acetate tapered dosage, and these mice have remained tumor-free In the oral heparin+oral hydrocortisone group, all mice remained tumor-free after their treatment was discontinued on day 47. The regimen of oral heparin+oral hydrocortisone seemed to be more effective for melanoma than it was for ovarian sarcoma or Lewis lung carcinoma.

(d) Bladder Carcinoma: 70 mice: 7 per group received a 1 mm$^3$ implant of tumor subcutaneously. All control animals died by day 31, with large primary tumors. No mice bearing bladder carcinoma developed lung metastases. One group was treated with oral heparin and subcutaneous cortisone acetate tapered dosage, starting on day 9 when mean tumor volume was 140 mm$^3$. Tumors stopped growing, but regressed only partially, and then reached a steady state where tumor volume remained at approximately 70 mm$^3$ for as long as the treatment was continued (i.e., 61 more days). Only one mouse died of pneumonia on day 19. The "dormant" tumors were viable, as evidenced by resumption of tumor growth whenever treatment was discontinued for one mouse at a time, beginning at day 70. For a second group treated with subcutaneous heparin and subcutaneous cortisone acetate 75 mg/kg as described above, the result was similar; i.e., long-term tumor "dormancy". One mouse died at day 21.

Because of the inability the standard regimen of oral heparin+cortisone acetate to bring about complete regression, higher concentrations of oral heparin were used with other groups. With oral heparin (600 U/ml)-cortisone acetate tapered dosage, there was more significant tumor regression and a steady state ("dormancy") was reached at a smaller tumor volume of approximately 45 mm$^3$. One mouse died. However, with 1000 U/ml heparin, there was complete regression; mice remained tumor-free after discontinuation of treatment on ay 39. No mice died in this group.

In summary, all tumors either stopped growing or regressed when the heparin-cortisone acetate combination was administered. In contrast, when either compound was used alone, tumor growth continued at the same rate as in animals receiving only saline injections; all such control animals died with a large tumor burden.

In the majority of animals treated with heparin+cortisone acetate, it was possible to achieve "complete regression", i.e., tumors did not recur after treatment was discontinued. Thus, with the most effective regimen, oral heparin (200 U/ml)+cortisone (s.c. 250-tapered dosage), it was possible to obtain "complete regression" in 100% of ovarian sarcomas, 100% of Lewis lung carcinomas and 80% of B-16 melanomas. However, when bladder carcinomas were treated with this regimen, there were no "complete regressions" until heparin was increased to 1000 U/ml, following which 100% of tumors regressed without recurrence. With the less effective regimen, heparin (s.c.)+cortisone (75 mgm), complete regression rate was ovarian, 80%; Lewis lung, 71%; B-16 melanoma 60%; and bladder 0%.

EXAMPLE 6

The hexasaccharide heparin fragment of Example 2 was dissolved in saline, 1.5 mg/ml. Three mice bearing implanted ovarian sarcoma were treated with subcutaneous injection of the hexasaccharide fragment twice daily at a dosage of 7 mg/kg and subcutaneous injection of cortisone acetate- tapered dosage. Control mice received either cortisone acetate alone or saline. While control tumors grew progressively, the hexasaccharide+cortisone acetate treated tumors regressed rapidly and were barely visible 4 days later. Their treatment with hexasaccharide was then discontinued, and the tumors reappeared 3–5 days later.

EXAMPLE 7

To directly observe avascular tumors during systemic therapy, Lewis lung tumors were implanted in the mouse cornea by the procedure of Muthukkaruppan et al., Science, Vol. 205, 1416–18 (1979) and treatment was begun 24 hours later. Heparin (oral)-cortisone acetate tapered dosage significantly inhibited capillary growth (0.02 mm/day) compared to cortisone acetate alone (0.24 mm/day), heparin alone (0.32 mm/day) or saline (0.23 mm/day). In the presence of heparin-cortisone acetate, a thin plate of tumor remained avascular. Three-dimensional tumor-growth did not occur. In contrast, in the saline controls or when either heparin or cortisone acetate were administered alone, tumors became vascularized and grew as a three-dimensional mass until they eventually perforated the cornea. These large tumors could be regressed to the flat, thin intracorneal phase by the resumption of the heparin-cortisone acetate combination. However, the intracorneal tumor cells could not be eradicated; discontinuation of the heparin-cortisone acetate led to recurrence of a vascularized tumor.

Lung metastases were counted in all animals that died. A ×6 stereoscope was used. In all control animals, the lungs were heavily studded with metastases from the three types of metastasizing tumors. In contrast, when any combination of heparin+cortisone acetate was used, no metastases were found in mice bearing ovarian sarcoma; only 1 metastasis was found in a mouse bearing Lewis lung carcinoma; and 2 avascular metastases less than 0.1 mm diameter were found in one mouse bearing B-16 melanoma. The nearly complete absence of metastases in heparin+cortisone treated mice was so striking, that the effect can be more readily appreciated by the following expression of data Total Number Lung Metastases

| Total Number Lung Metastases | |
|---|---|
| Controls = | 4553 in 73 animals |
| Heparin + Cortisone = | 3 in 39 animals |

Furthermore, no lung metastases appeared in any surviving animals that were off treatment.

To exclude the possibility that tumor regression might be caused by direct cytotoxicity, all 4 types of tumor cells were cultured in the presence of 10% serum obtained from mice receiving either heparin, cortisone acetate, heparin-cortisone acetate, or no drug. Heparin-cortisone acetate did not inhibit cell growth, but in fact stimulated it. Furthermore, histological sections shows no evidence of a cytotoxic effect on bone marrow or intestinal mucosa in animals receiving heparin-cortisone acetate.

To exclude the possibility that heparin-cortisone acetate might induce tumor regression by promoting an immune reaction, mice were inoculated with fresh tumor cells at various intervals after they were off treatment. These tumors grew at the same rate as the original implants. Furthermore, if tumor regression was nearly complete and heparin-cortisone acetate was discontinued prematurely, the original tumor resumed its growth. Finally, by stopping and starting treatment, or by using sub-optimal doses of heparin-cortisone, bladder tumors could be maintained at nearly a constant small size (i.e., 45 to 70 mm$^3$) for periods of more than 8 weeks.

Inflammatory angiogenesis induced by implantation of silica particles into the rabbit cornea, immune angiogenesis induced by implantation of lymph node from a different rabbit, were also completely prevented by the cortisone-heparin pellets. Cortisone by itself temporarily delayed the onset of both types of angiogenesis (compared to an empty pellet), and heparin by itself delayed the onset of immune angiogenesis, but neither alone prevented angiogenesis for an extended period of time as did the cortisone-heparin combination.

EXAMPLE 8

A human colon carcinoma was inoculated subcutaneously into nude [athymic] mice, and allowed to grow to a volume of 0.5 cm$^3$. Controls and treated animals received the same compounds, except that heparin in the drinking water was 1000 U/ml. also an additional treatment group included oral hydrocortisone (0.45 mg/ml) and oral heparin. Animals were housed in cages protected by millipore filter. Tumors grew progressively in all control animals, but regressed in animals treated with heparin and cortisone or heparin and hydrocortisone. The treated tumors were barely palpable after 6 weeks of therapy.

EXAMPLE 9

CD-1 "Swiss" mice were used because this strain breeds easily and the fertilized females almost always conceive and subsequently deliver a full litter.

One male was left alone in the cage for 24 hours. His bedding was then changed and two females were added at 5 p.m. The females were then checked at 8 a.m. the next morning for the presence of a cervical plug, which indicates insemination. Sufficient male-female cages were set up to obtain at least 20 pregnant females.

Treatment of the inseminated females was started on the day after insemination by offering drinking water to each of four groups, as follows:

| Group I | Heparin (Hepar) 1,000 U/ml in water |
|---|---|
| II | Hydrocortisone phosphate, 0.45 mg/ml in water |
| III | (I) and (II) together in water |
| IV | Water alone |

The treatments were continued for only four days, after which female mice were placed one per cage, and followed closely for the presence of offspring. The cages were checked daily for any sign of abortion (fur, fetal remains, etc.).

Groups I, II and IV all produced healthy litters. In Group III there were no mice born and no evidence of abortion. This supports the conclusion that anti-angiogenesis by heparin-cortisone inhibits implantation, presumably by inhibiting capillary growth from the uterus.

EXAMPLE 10

Inhibition of Tumor Vessels in the Rabbit Cornea

17α,21-Dihydroxypregna-4,9(11)-diene-3,20-dione (or delta-9(11)-deoxycortisol) (90 mg/ml) and Sigma heparin (1.8 mg/ml) were dissolved in 2 cc of 10% ethylene vinyl acetate (EVA) copolymer. A 1–2 mm pellet was cut from the polymer and implanted into the pocket of a rabbit cornea 1 mm from the limbus. The polymer was positioned between the limbal vessels and a 1 mm³ piece of V2 Carcinoma implanted distal to the pellet. The opposite eye of each of the 3 rabbits tested contained empty polymers. Mean vessel growth or 0.45 mm/day over a period of 16 days was seen with the control corneas and 0.07 mm/day was seen in the eyes containing steroid and heparin Measurements are expressed as the mean±SD. Similar results have been demonstrated with cortexolone and heparin implanted in the same manner.

What is claimed is:

1. A composition for treating mammals for stopping growth, bringing about regression, or preventing metastasis of solid tumors in mammals by oral, or parenteral administration in which the active agents consist essentially of effective proportions for said treating of (1) a member selected from the group consisting of a said composition including a non-toxic physiologically acceptable carrier adapted for oral or parenteral administration, said composition exhibiting an avascular zone when implanted in an immature chick chorioallantoic membrane. heparin fragment which is either a hexasaccharide or larger oligosaccharide and an analogous compound having of the structures

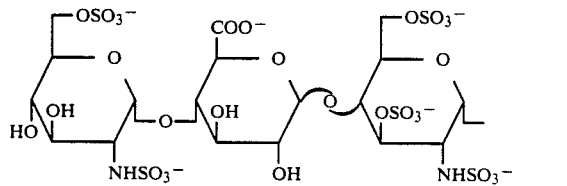

or

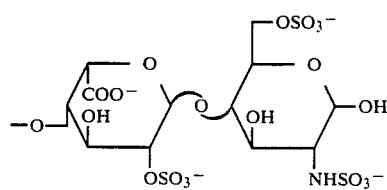

or

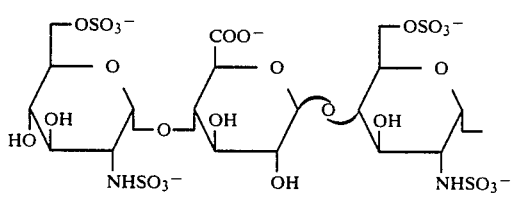

or

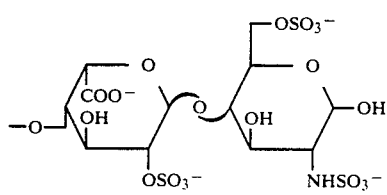

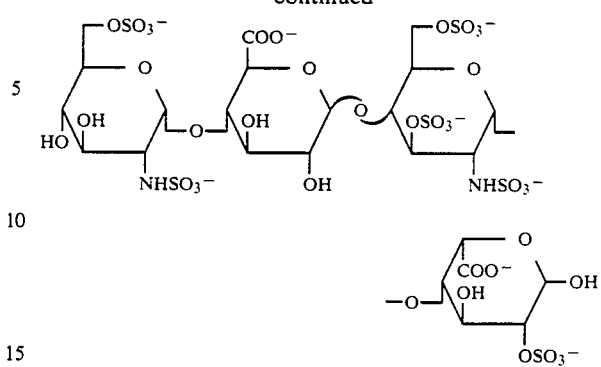

and (2) a member selected from the group consisting of steroids having a 17α- and 21-hydroxy groups, 3- and 20-one groups, and in the 16-position hydrogen, hydroxy, or a methyl group, and a non-toxic physiologically acceptable carboxylate, or acetal, or ketal, or phosphate thereof.

2. A composition as claimed in claim 1 in which the active agents consist essentially of a heparin fragment which is either a hexasaccharide or larger oligosaccharide and cortisone.

3. A composition as claimed in claim 1 in which the active agents consist essentially of a heparin fragment which is either hexasaccharide or larger oligosaccharide and hydrocortisone.

4. A composition for treating mammals for stopping growth, bringing about regression, or preventing metastasis of solid tumors in mammals by oral administration only, in which the active agents consist essentially of effective proportions for said treating of (1) a member selected from the group consisting of heparin and a heparin fragment which is either a hexasaccharide or larger oligosaccharide and an analogous compound having one of the structures

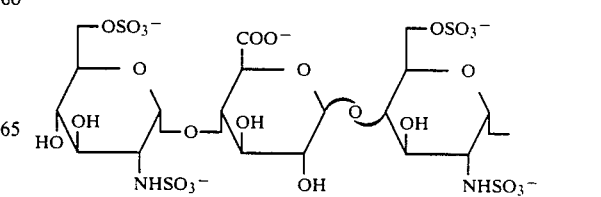

or

-continued

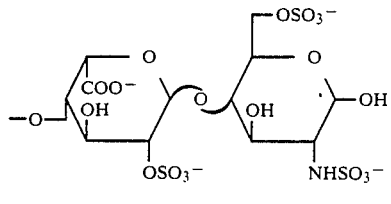

or

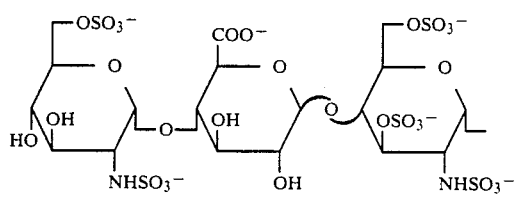

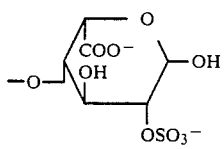

and (2) a member selected from the group consisting of steroids having 17α- and 21-hydroxy groups, 3- and in the 16-position hydrogen, hydroxy, or a methyl group, and a non-toxic physiologically acceptable carboxylate, or acetal, or ketal, or phosphate thereof, said composition including a non-toxic physiologically acceptable carrier adapted for oral administration only. said composition exhibiting an avascular zone when implanted in an immature chick chorioallantoic membrane.

5. The composition as claimed in claim 4 in which the active agents consist essentially of (1) heparin and (2) cortisone.

6. The composition as claimed in claim 4 in which the active agents consist essentially of (1) heparin and (2) hydrocortisone.

7. A method of treating mammals bearing solid tumor masses to stop growth, to bring about regression or to prevent metastasis thereof which comprises administering orally thereto a dose effective for said treating of active agents consisting essentially of (1) heparin or a heparin fragment which is a hexasaccharide or larger oligosaccharide or an analogous compound having one of the structures

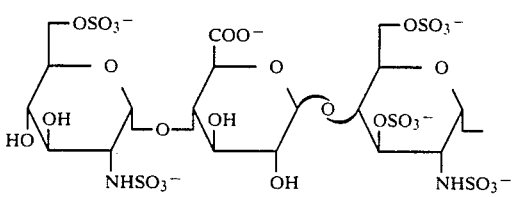

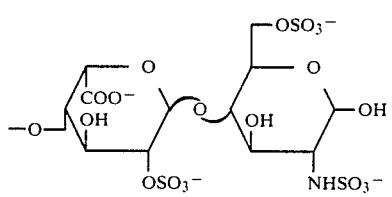

or

-continued

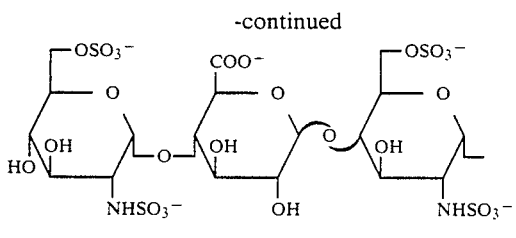

or

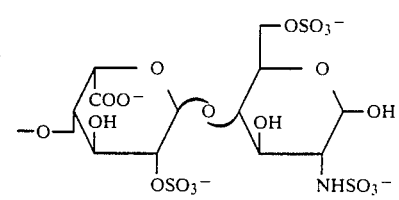

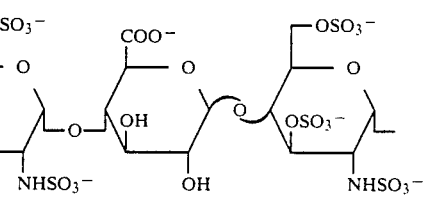

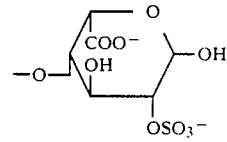

and (2) a steroid having 17 α- and 21-hydroxy groups, 3- and 20-one groups, and in the 16- position hydrogen, hydroxy, or a methyl group, and a non-toxic physiologically acceptable carboxylate, or acetal, or ketal, or phosphate thereof, wherein said tumor masses are susceptible to said treatment with said active agents.

8. The method as claimed in claim 7 in which administration is oral and the active agents consists essentially of heparin and hydrocortisone.

9. The method as claimed in claim 7 in which administration is oral and the active agents consist essentially of a hexasaccharide heparin fragment and hydrocortisone.

10. The method as claimed in claim 7 in which said administration is oral and said active agent (1) is heparin.

11. A method of treating mammals bearing solid tumor masses to stop growth, to bring about regression or to prevent metastasis thereof which comprises administering thereto an effective dose effective for said treating of active agents consisting essentially of (1) a heparin fragment which is either a hexasaccharide or larger oligosaccharide or an analogous compound having one of the structures

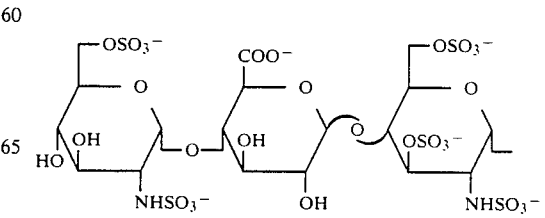

-continued

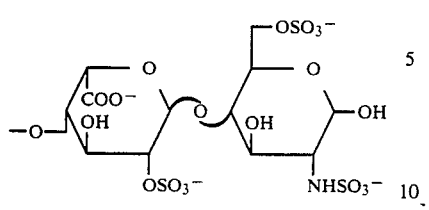

or

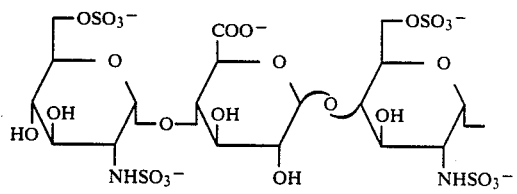

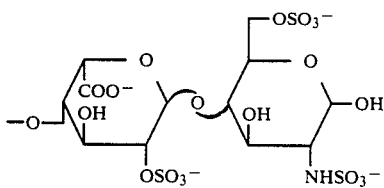

or

-continued

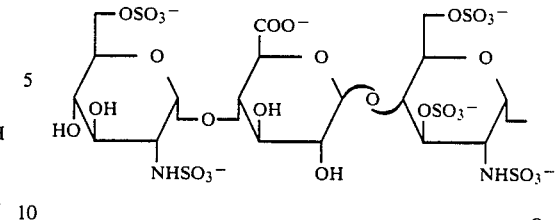

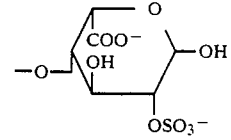

and (2) a steroid having 17α- and 21-hydroxy groups, 3- and 20-one groups, and in the 16- position hydrogen, hydroxy, or a methyl group, and a non-toxic physiologically acceptable carboxylate, or acetal, or ketal, or phosphate thereof, wherein said tumor masses are susceptible to said treatment with said active agents.

12. The method as claimed in claim 11 in which the active agents consist essentially of (1) either said heparin fragment or analogous compound and (2) cortisone.

13. The method as claimed in claim 11 in which the active agents consist essentially of (1) said heparin fragment and (2) cortisone.

14. The method as claimed in claim 11 in which the active agents consists essentially of (1) either said heparin fragment or analogous compound and (2) hydrocortisone.

15. The method as claimed in claim 11 in which said active agents consist essentially of (1) said heparin fragment and (2) hydrocortisone.

* * * * *

UNITED STATES PATENT AND TRADEMARK OFFICE
CERTIFICATE OF CORRECTION

PATENT NO. : 4,994,443

DATED : February 19, 1991

INVENTOR(S) : Moses J. Folkman, Stephanie Taylor and Robert S. Langer

It is certified that error appears in the above-identified patent and that said Letters Patent is hereby corrected as shown below:

Col. 4, lines 59-60, no new paragraph at line 60, which should follow immediately after "of" in line 59;

Col. 6, line 9, "NH" should be --$NH_4$--;

Col. 9, line 49, after "water" insert a period;

Col. 10, line 1, after "free" insert a period;

Col. 13, line 6, "or" should be --of--;
line 9, after "heparin" insert a period;

Col. 13, claim 1, lines 21-26, delete "said compostion including a non-toxic physiologically acceptable carrier adapted for oral or parenteral administration, said composition exhibiting an avascular zone when implanted in an immature chick chorioallantoic membrane";

Col. 14, claim 1, line 22, after "thereof" begin a new paragraph and insert
--said composition including a non-toxic
physiologically acceptable carrier adapted for
oral or parenteral administration,
said composition exhibiting an avascular zone when
implanted in an immature chick chorioallantoic
membrane.--;

UNITED STATES PATENT AND TRADEMARK OFFICE
CERTIFICATE OF CORRECTION

PATENT NO. : 4,994,443

DATED : February 19, 1991

INVENTOR(S) : Moses J. Folkman, Stephanie Taylor and Robert S. Langer

It is certified that error appears in the above-identified patent and that said Letters Patent is hereby corrected as shown below:

Col. 14, claim 3, line 30, after "either" insert --a--.

Col. 15, claim 4, line 28, after "3-" insert --20-one groups--.;

line 31, after "thereof" begin a new paragraph;

line 33, after "only" change "." to --,-- and begin a new paragraph.

Signed and Sealed this

Twenty-third Day of February, 1993

Attest:

STEPHEN G. KUNIN

*Attesting Officer*     *Acting Commissioner of Patents and Trademarks*